May 14, 1974 E. CULLY Plant Pat. 3,547
BALD CYPRESS
Filed Dec. 27, 1971
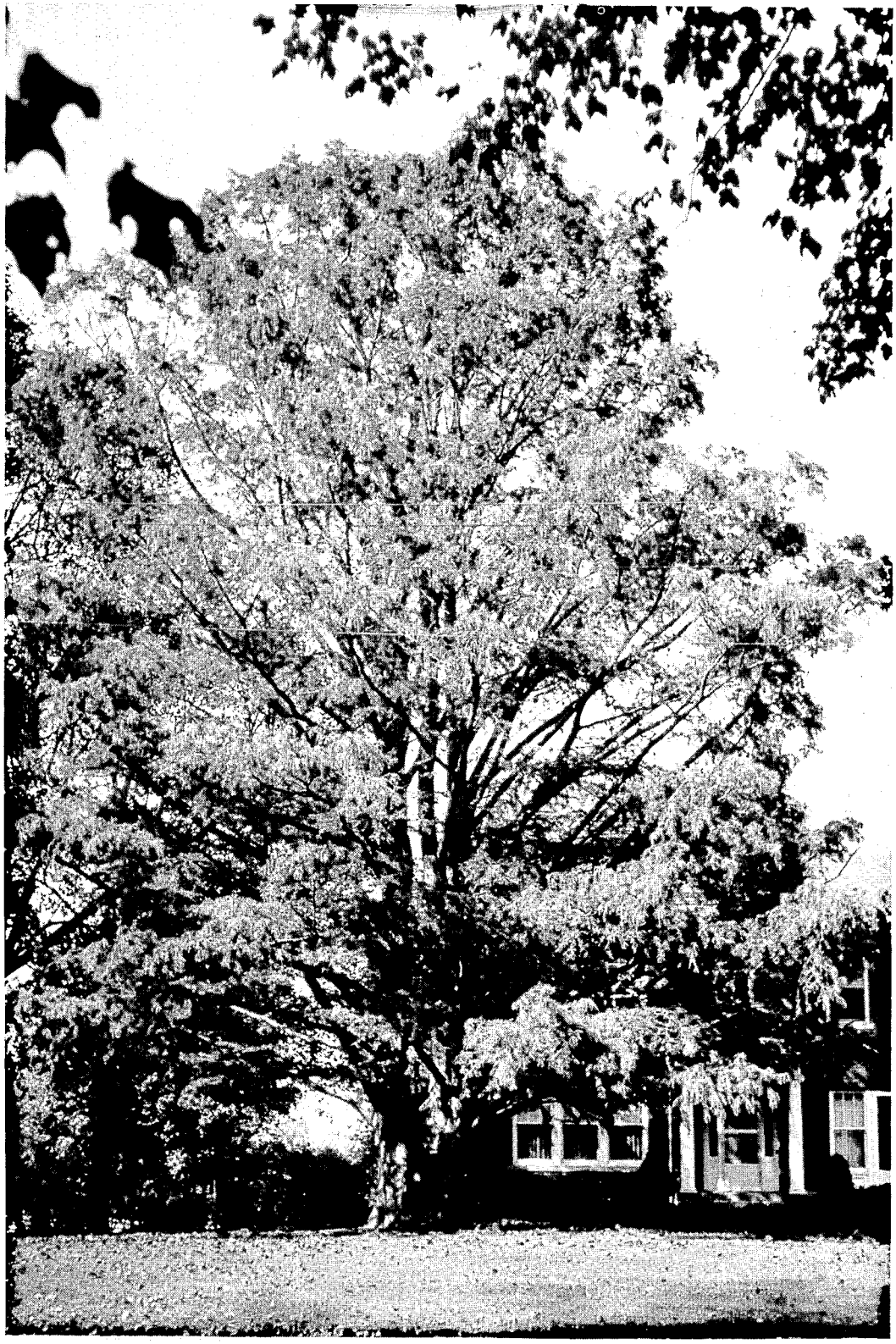

United States Patent Office

Plant Pat. 3,547
Patented May 14, 1974

3,547

BALD CYPRESS TREE

Earl Cully, R.R. 5, Jacksonville, Ill. 62650

Filed Dec. 27, 1971, Ser. No. 212,827
Int. Cl. A01h *7/00*
U.S. Cl. Plt.—50 1 Claim

ABSTRACT OF THE DISCLOSURE

This disclosure concerns a new and distinct variety of *Taxodium distichum* (L.) (commonly known as bald cypress) characterized by its rapid growth, abundant forking of stem from near to the ground and strong growth of lateral branches resulting in a multibranched large tree with a crown diameter approaching 80% of its height.

BACKGROUND OF THE INVENTION

This new variety of bald cypress was discovered by me in Pittsfield, Illinois, in Pike County, in a cultivated home lawn that has grown to a height of 85 to 90 feet. During the past two years, I have grafted many cuttings, from this parent tree to other bald cypress trees. At present, I have over 1,000 grafts and all are growing true to form and have rapid growth in the Cully Nursery in Jacksonville, Illinois.

DESCRIPTION OF THE DRAWING

My new variety of bald cypress is shown in the accompanying drawing.

DESCRIPTION OF THE NEW PLANT VARIETY

The following is a detailed description of my new variety of bald cypress.

Origin: Seedling.
Parentage: Unknown.
Classification: Gymnospermae, Pinaceae (Taxodiaceae).
*Botanic.—Taxodium distichum* (L.).
Form: Tree.
Shape: Large, massive spreading crown.
Height: 85 to 90 feet at full growth.
Trunk size: 6 feet in diameter at breast height at full growth.
Growth rate: Rapid; 2 to 3 feet per year.
Strength: Strong, excellent grower.
Bark: Typical.
Branches:
*Angle of attachment.*—30 to 35 degrees above horizontal.
*Spacing.*—24 to 30 inches apart.

*Size.*—Typical.
*Bark.*—Typical.
Leaves:
*On deciduous branches.*—Two ranked, alternate; smaller on late growth.
*Length.*—1 to 1.5 centimeters.
*Form.*—Linear, lanceolate, apiculate.
Flowers: Male and female strobiles.
*Blooming period.*—Typical for species, i.e., March and April in Illinois.
Fruit: A cone typical of the species.
*Maturity period.*—October and November in Illinois.
*Size.*—Mixed.
*Axial diameter.*—To 1½ inches.
*Traverse diameter.*—To 1⅛ inches.
*Form.*—Rounded cone; with about 25 scales variable in size.

This new variety resembles in growth habit some old Mexican specimens of Montezuma cypress or ahuehuete (*T. ascendens*) but differs in the foregoing specific botanical characters, deciduous nature and much greater cold tolerance. It has a very attractive appearance and is a massive ornamental shade tree. It further differs from other seedlings and grafted trees of its species in its rapid growth, abundant forking of the stem from near the ground, its strong growth of lateral branches resulting in a multibranched large tree with a crown diameter approaching 80% of its height.

I claim:

1. A new and distinct variety of bald cypress tree (Gymnospermae, Pinaceae) (Taxodiaceae) substantially as shown and described, characterized particularly as to novelty by its rapid growth, abundant forking of the stem near the ground strong growth of lateral branches resulting in a multibranched, large, massive tree with a crown diameter approaching 80% of its height, and its tolerance to cold weather.

References Cited

The First Plant Patents, Allyn, Educ. Found. Inc. 1934, pp. 67–69, relied on.
The Standard Cyclo. Bailey, 1935, p. 3314 relied on.
Trees for Amer. Gardens, Wyman, 1951, p. 327 relied on.
New Illus. Ency. of Gard., Everett, 1960, p. 2249 relied on.
Manual of Cultivated Trees and Shrubs, Rehder, 1960, p. 499, relied on.

ROBERT E. BAGWILL, Primary Examiner